United States Patent [19]

McEntire et al.

[11] Patent Number: 5,750,770

[45] Date of Patent: May 12, 1998

[54] UNSATURATED MONO-ESTERS AND THEIR USE IN COATING COMPOSITIONS

[75] Inventors: Edward E. McEntire, Hampton Township, Allegheny County; Lyle L. Foringer, West Franklin Township, Armstrong County, both of Pa.

[73] Assignee: PPG Industries, Inc., Pittsburgh, Pa.

[21] Appl. No.: 541,748

[22] Filed: Oct. 10, 1995

[51] Int. Cl.$^6$ ..................................................... C07C 67/26
[52] U.S. Cl. ................................................ 560/200; 560/209
[58] Field of Search ........................................ 560/200, 209

[56] References Cited

U.S. PATENT DOCUMENTS

| | | | |
|---|---|---|---|
| 3,391,183 | 7/1968 | Dowbenko | 260/485 |
| 3,481,973 | 12/1969 | Wygant et al. | 260/485 |
| 4,166,893 | 9/1979 | Kambanis et al. | 526/75 |
| 5,418,306 | 5/1995 | Shalati et al. | 526/329.1 |
| 5,418,307 | 5/1995 | Valpey, III et al. | 526/329.1 |

FOREIGN PATENT DOCUMENTS

| | | |
|---|---|---|
| 0507192 | 6/1971 | Switzerland . |
| 507192 | 6/1971 | Switzerland . |

OTHER PUBLICATIONS

English Abstract of 0507192.
Chemical Abstracts, vol. 58, Columns 14935 and 14936.
B.C. Trivedi and B.M. Culbertson, "Maleic Anhydride", 1982 Plenum Press, New York and London, Chapter 3 Reactions of Functional Groups, pp. 78 thru 81.
Chem Ber. 119, 3492–3497 (1986).

*Primary Examiner*—Joseph L. Schofer
*Assistant Examiner*—Wu C. Cheng
*Attorney, Agent, or Firm*—Dennis G. Millman

[57] ABSTRACT

Hydroxy functional, unsaturated diesters are disclosed that comprise the esterification reaction products of unsaturated anhydrides with secondary alcohols to form monoesters, followed by oxyalkylation of the monoester with epoxy compounds, whereby a diester is formed with hydroxy functionality. Use of secondary alcohol yields monoesters less prone to disproportionation. The unsaturated diesters may be copolymerized with vinyl monomers to form hydroxy functional copolymers useful in coating applications, wherein they may be included in compositions along with a curing agent that is reactive with hydroxy groups.

8 Claims, No Drawings

1

UNSATURATED MONO-ESTERS AND THEIR USE IN COATING COMPOSITIONS

BACKGROUND OF THE INVENTION

This invention involves unsaturated monoester monomers that find utility in coating compositions. Unsaturated monoesters are useful intermediates in that they may be modified by further esterification to form diesters and/or by copolymerization with vinyl monomers to form polymers. These polymers, when provided with crosslinking functionality, such as hydroxyl groups, are useful in the coating industry since they can be cured to form durable coatings by reaction with crosslinking agents that are reactive with the hydroxyl groups, such as polyisocyanates, aminoplasts, and anhydrides.

A drawback to the use of unsaturated monoesters is their instability, particularly at moderately elevated temperatures. This instability is due to the tendency for the monoesters to disproportionate to the diacid, the diester, and sometimes also the acid anhydride. As a result, the amount of monoester present in the starting material being used for a polymerization may vary, and unwanted impurities may be present. These variations and impurities make the polymerization less controlled and lead to side reactions that dilute the desired polymer product. It would be desirable to have available monoesters having greater stability.

Unsaturated monoesters are readily made by the reaction of unsaturated anhydrides (most commonly maleic anhydride) with alcohols. Primary alcohols have been preferred for this purpose by the prior art due to their reported rapid rate of reaction. In the text *Maleic Anhydride* by B. C. Trivedi and B. M. Culbertson (Plenum Press, New York and London, 1982) at pages 78–79, several primary alcohols are disclosed for forming monoesters with maleic anhydride, but the one secondary alcohol (isopropyl alcohol) mentioned is reported to have no reaction.

SUMMARY OF THE INVENTION

In accordance with the present invention, unsaturated monoesters having improved stability are provided by reacting an anhydride with a secondary alcohol. Monoesters made in this manner have been surprisingly found to be considerably less prone to disproportionation reactions than monoesters made with primary alcohols.

These monoesters may be used to make unsaturated diesters by reaction of the remaining acid group. Particularly advantageous is the formation of an unsaturated diester by oxyalkylation of the monoester with an epoxy compound whereby the second ester group has hydroxy functionality. Because the monoester of the present invention has a high degree of stability, the subsequent reaction yields the desired diester with a high degree of purity.

The unsaturated, hydroxy functional diesters made in accordance with the above procedure of the present invention may be used as monomers for various copolymerizations. For example, such monomers can be copolymerized with a vinyl compound to produce a useful hydroxy functional copolymer having hydroxyl functional groups and non-hydroxy containing groups. Hydroxyl functionality spaced along the length of the polymer is advantageous in coating compositions for crosslinking with hydroxy group-reactive curing agents such as isocyanates, aminoplasts, or anhydrides. Such coating compositions are characterized by good mar resistance and are the subject matter of co-pending, commonly owned U.S. patent application Ser. No. 08/541.993 titled "UNSATURATED HYDROXY DIESTER COPOLYMERS AND THEIR USE IN COATING COMPOSITIONS" filed on even date herewith by Gregory J. McCollum, Karl F. Schimmel, James A. Claar, Joseph M. Carney, Stephen J. Thomas, and Leigh Ann Humbert.

DETAILED DESCRIPTION

Unsaturated anhydrides are the preferred starting material for the present invention for their ability to form alternating copolymers with vinyl monomers. Maleic anhydride is preferred due to its availability, but other substituted or unsubstituted anhydrides of dicarboxylic acids may be used. These include, for example, citraconic anhydride, dimethyl maleic anhydride, chloro maleic anhydride, dichloro maleic anhydride, and itaconic anhydride. Any unsaturated anhydride having alkyl, aryl, or other substitution may serve the same purpose. Alternatively, a diester of maleic acid or another unsaturated dicarboxylic acid may be used as the starting material, whereby the diester is subsequently transesterified to provide a hydroxy functional ester group.

The esterification of the anhydride is carried out in two stages. First, the anhydride is opened with a secondary alcohol to form a monoester. In the second stage, the monoester is oxyalkylated with an epoxy compound, preferably alkylene oxide, whereby a diester is formed, with the second ester group containing a hydroxy group as a product of the reaction with the epoxide.

Any alcohol may serve to open the anhydride ring in the first stage of the esterification. The improved stability that characterizes the monoesters of the present invention was found to be attained when secondary alcohols are used for this stage. Since the primary function of this alcohol is merely to open the anhydride, a wide selection of secondary alcohols may be used, including secondary alkyl and cycloalkyl alcohols in general. The use of simple alcohols is preferred, preferably selected from the group consisting of 2-propanol, 2-butanol, cyclohexanol, and mixtures thereof. Ether alcohols may also be used.

Oxyalkylating the monoester to a diester is accomplished by reaction with an epoxy compound, particularly an alkylene oxide such as ethylene oxide or propylene oxide. The use of propylene oxide is preferred in that it forms a 2-hydroxy group in the ester group. Materials containing glycidyl groups may also be used to open the anhydride, such as alkyl or aryl glycidyl ethers (e.g., butyl glycidyl ether, phenyl glycidyl ether).

The resulting hydroxy functional, unsaturated diester may serve as a monomer to be polymerized or copolymerized with other unsaturated monomers to form hydroxy functional polymers which are useful in coatings and other applications.

More specifically the unsaturated diester may be copolymerized with vinyls—either a single type of vinyl or a combination of different vinyls. The vinyls are chosen such that they are capable of producing a substantially alternating copolymer with the unsaturated diester. Typically, the vinyl monomer component is selected from the group consisting of alpha-olefins, vinyl aromatic compounds or substituted vinyl aromatic compounds, allyl compounds, vinyl ethers, vinyl esters, vinyl acetals, and mixtures thereof. In some embodiments, a combination of alpha-olefin and vinyl aromatic monomer (e.g., styrene) are used in approximately equal molar amounts to copolymerize with the diester. Acrylic and methacrylic compounds may also be included among the vinyl compounds usable in the copolymerization. Other electron deficient monomers such as dialkyl maleate or dialkyl fumarates may be part of the co-monomer component to be copolymerizied with the hydroxy functional unsaturated diester monomer. These may include dimethyl maleate, dibutyl maleate, dibutyl fumarate, dibenzyl fumarate, ethyl methyl maleate, and the like.

Alpha-olefins useful as co-monomers include the lower alpha-olefins, that is, materials with a carbon chain length of less than 20, preferably those with 2 to 12 carbon chain length, most preferably 3 or 4 to 10. Carbon chain lengths above 10 may be used, but are not preferred because they are not as easily handled during processing. Specific examples include ethylene, propylene, isobutene, diisobutylene, 1-hexene, 1-octene, and 1-decene, and mixtures thereof, with the preferred materials being propylene, isobutylene, 1-hexene, and 1-octene. Cycloaliphatic olefins are also suitable and include, for example, cyclobutene, cyclopentene, 1-methylcyclopropene, methylenecyclopentene, cyclohexene, cycloheptene, cyclooctene, and mixtures thereof.

Vinyl monomers for use as co-monomers may be chosen from aromatic vinyl monomers, preferably styrene, also including substituted styrene compounds. Examples of alpha-substituted vinyl aromatic compounds include vinyl toluene, alpha-methylstyrene, p-isopropyl-alpha-methylstyrene, p-isopropylstyrene, p-methoxy-alpha-methylstyrene, p-methoxystyrene, p-chloro-alpha-methylstyrene, p-chlorostyrene, p-fluoro-alpha-methylstyrene, p-fluorostyrene, p-dimethylamino-alpha-methylstyrene, p-dimethylaminostyrene, and the like. Beta-substituted styrene compounds can also be used, such as stilbene, beta-methylstyrene, beta-chlorostyrene, beta-methoxymethylstyrene, beta-methoxystyrene, beta-n-butoxystyrene, beta-isobutoxystyrene, beta-tert-butoxystyrene, p-methoxy-beta-methylstyrene, p-methyl-(beta-methylstyrene), p-chloro-beta-methylstyrene, and the like.

Another class of vinyl monomers that may be used are vinyl ethers, which may contain alkyl, aryl or cycloaliphatic groups with a carbon chain length of 1 to 20. Specific examples of vinyl ethers include alkyl vinyl ethers such as methyl, ethyl, isopropyl, 2-ethylhexyl, n-butyl, isobutyl, tert-butyl, 2-chloroethyl, benzyl vinyl ethers, and mixtures thereof. Also suitable are aryl vinyl ethers including methyl propenyl ether (both cis and trans isomers), phenyl vinyl ether, and mixtures thereof. Additionally, 2-phenylvinyl alkyl ethers or thioethers having a carbon chain length not exceeding about 6 wherein the alkyl group can be either straight-chain or branched can be used. Suitable cycloaliphatic vinyl ethers include cyclopentyl and cyclohexyl vinyl ethers, and mixtures thereof. Additional examples of suitable vinyl ether monomers include divinyl ether, 1,2-dimethoxyethylene, p-dioxene, and conjugated dihydroanisole, and mixtures thereof. Information regarding copolymerization of vinyl ethers may be found in J. Poly. Sci., Vol. 48, page 279 (1960) and in *Maleic Anhydride* by B. C. Trivedi and B. M. Culbertson (Plenum Press, New York and London, 1982).

The unsaturated co-monomer may also be selected from allyl compounds including allylbenzene, 2-allylphenol, alpha-allylnaphthalene, 3-allylcyclopentene and mixtures thereof. Functionalized allyl compounds bearing functional groups including hydroxyl, amino, cyano, carboxyl, silane, phosphonate, epoxy, and ether moieties include allyl alcohol, methallyl alcohol, 2-phenylallyl alcohol, 2-methylene propanediol, 1,1-dimethylallyl alcohol, methallylamine, N-allylacetamide, allyl acetate, trimethylallylsilane, and diethyl acetonyallylphosponate, N-allylamidazole, 2-allylpyrrole and mixtures thereof. When an ether group is present on the allyl compound, the ether group can be a functionalized or non-functionalized alkyl, aryl, or cycloaliphatic species. Specific examples include allyl glycidyl ether, heptafluoroisopropyl allyl ether, heptafluoroisopropyl methallyl ether, allyl acetone, methallylacetone, 2-allylcyclohexanone, 1-phenyl-4-pentene-1-one, diallyl ether, and mixtures thereof.

It should be understood that the unsaturated vinyl monomer component employed to copolymerize with the hydroxy functional, unsaturated maleate ester can comprise mixtures of two or more of any of the monomers described above.

The vinyl co-monomer component and the diester component described above characteristically react to produce an alternating copolymer rather than a random copolymer. In those embodiments in which this alternating feature is desired, it may be preferred when synthesizing the alternating copolymer to discourage the formation of repeating units of vinyl monomer. Additionally, it may be desirable to control the molecular weight of the alternating copolymer. Typically, this is achieved by "starving" the reaction, that is, by adding an amount of initiator to the diester prepared above, then slowly and continuously adding additional initiator and the vinyl monomer component to the reaction vessel at a controlled rate such that self-polymerization of the vinyl monomer component is discouraged. When this procedure is followed, it is believed that the reaction product is predominantly an alternating polymer represented by the structural formula $(A_xB_y)_m$, where A represents a single unit comprising a diester, B represents a single unit comprising a vinyl monomer, x and y are equal to 1, and m is an integer larger than 1. In other words, the formation of alternating copolymers where either x or y, or where both x and y, are integers larger than 1 is discouraged. It is theoretically possible that some portions along the copolymer chain contain repeating units of vinyl monomer; however, it is believed that these areas may be essentially eliminated by adjusting the feed rates of the initiator and the vinyl monomer component. Minor amounts of repeating units may not have a perceptible effect on the results, and therefore may be tolerated.

After all the vinyl monomer component has been added, the reaction mixture is usually held at the reaction temperature for a period of time ranging from about 30 minutes to about 8 hours, preferably from about 60 minutes to about 90 minutes, to ensure the reaction is complete. The resultant copolymer solution generally has solids content, determined at 110° C. for 60 minutes, of from about 40 percent to about 95 percent, preferably from about 60 percent to about 80 percent by weight.

The copolymer of the present invention generally has a number-average molecular weight of from about 1,000 to about 100,000, preferably from about 1,000 to about 5,000, more preferably from about 1,000 to about 3,500 as measured by gel permeation chromatography using polystyrene as standard.

The copolymers described above are useful as film-forming binders for coating compositions when combined with a curing agent. Typical crosslinking compounds well known to those skilled in the art as curing agents include, isocyanates, aminoplasts such as melamine-formaldehydes and benzoguanamines, and anhydrides. The coating composition may be a one-package composition, in which case the curing agent is heat-activated, such as a blocked isocyanate or the aminoplasts. These polymers particularly lend themselves to use in two-package, room temperature curing compositions, wherein the hydroxy functional copolymer is contained in one package and the curing agent, e.g., a polyisocyanate, is contained in a separate package. Optionally, a third package may additionally be employed comprising a viscosity reducer. The separate packages are blended immediately prior to application of the coating composition onto a substrate. The ability to form a durable, mar resistant coating having good appearance at or only slightly above room temperature is particularly useful for automotive refinish applications.

The coatings of the present invention may be clear or colored, and may serve as primers, base coats, or topcoats, including as a clear topcoat applied over a colored base coat. When the composition is used as a clear coat in a color plus clear composit coating, pigmented base coat is first applied to the substrate. The base coat is then "flashed," that is, left to stand at temperatures ranging from ambient temperature to 80° C. for about 10 seconds to 30 minutes, before a clear topcoating composition is applied to it. Base coat compositions are those well known in the art as described, for example, in U.S. Pat. No. 4,681,811.

If the coating composition is to be a colored coating, it may include a pigment component of a known type. The pigment component can contain inorganic, organic, metallic, metallic-effect, filler and anti-corrosive pigments, and mixtures thereof. Suitable inorganic pigments include titanium dioxide, iron oxide, lead chromate, chrome green, cadmium sulfide, lithopone pigments, and the like. Suitable organic pigments include carbon black; monoazo, diazo, and benzimidazolone yellows, oranges, reds, and browns; phthalocyanine blues and greens; anthraquinone pigments ranging from yellow to blue; quinacridone yellows, reds and violets; perylene reds and browns; indigoid reds, blues, and violets; thioindigo violets; isoindolinone yellows, oranges and reds; quinoline yellows, and the like. Suitable metallic and metallic-effect pigments include aluminum, zinc, lead, bronze, copper, stainless steel and mica flake, and the like. Suitable filler pigments include magnesium silicate clays, fumed or precipitated silicas, barytes, blanc fixe, china clay, and the like. Suitable anti-corrosive pigments include lead oxide, zinc chromate, zinc phosphate, micaceous iron oxide, and the like. Mixtures containing any of the pigments described above are also suitable.

Optionally, the coatings may further contain a diluent. The diluent serves to reduce the viscosity of the dispersion and to assist in pigment wetting. Typically, the diluent comprises an organic solvent. Suitable organic solvents include ketones such as methyl isobutyl ketone, methyl ethyl ketone, diisobutyl ketone, and the like; esters such as butyl acetate, isobutyl acetate, pentyl propionate, and the like; alcohols such as methanol, ethanol, propanol, butanol, isobutanol, and the like; or glycol ethers such as the monoalkyl ethers of ethylene glycol, diethylene glycol, or propylene glycol, and the like.

Although organic solvents are the preferred diluents, suitable alternative diluents include nonreactive oligomeric or polymeric materials with a viscosity ranging from about 20 centipoise to about 1,000 centipoise as measured with a Brookfield viscometer at about 72° F. (22° C.) and a glass transition temperature lower than about 35° C. as measured by any of the common thermal analytical methods well understood by those skilled in the art. Specific examples include plasticizers such as tributyl phosphate, dibutyl maleate, butyl benzyl phthalate, dibutyl benzyl phthalate and mixtures thereof; and silane compounds such as vinyl trimethoxy silane, gamma-methacryloxypropyl trimethoxy silane, and mixtures thereof.

Mixtures of organic solvents or mixtures of organic solvents with the nonreactive oligomeric or polymeric diluents may also be used, provided there is no phase separation when the diluents are mixed with the copolymer of the present invention. When present, the diluent is generally used at a level of from about 0.1 percent to about 500 percent, preferably from about 20 percent to about 400 percent, more preferably from about 50 percent to about 200 percent by weight, the percentages based on the weight of solids (resin and pigment) present in the composition.

Optionally, the coatings may contain an auxiliary polymer. The purpose of the auxiliary polymer is to modify the properties of the coating composition. For example, it is often desirable to increase the solids level of a pigment dispersion or a coating composition without producing a large increase in viscosity. Or it may be desirable to modify the pigment wetting characteristics of the vehicle used to prepare the pigment dispersion. Similarly, it is often desirable to modify certain physical properties of the coating composition to which the pigment dispersion is subsequently added, for example the appearance, gloss, humidity resistance, mar resistance or chemical resistance of the cured film. A variety of materials are suitable for use as the auxiliary polymer. These include, but are not limited to, acrylic polymers, polystyrene polymers, acrylonitrile polymers, polyester polymers, epoxy polymers, polyamide polymers, butadiene polymers, polyalkylene polymers, polyalkylene glycol polymers, aminoplast resins, polyurethane polymers, polysilane polymers, polysiloxane polymers, and the like. Additionally, the auxiliary polymer may contain functional groups including but not limited to hydroxyl groups, carboxyl groups, amino groups, epoxy groups, phosphate groups, and the like. Mixtures of auxiliary polymers are also appropriate. Methods for preparing such auxiliary polymers are well understood by those skilled in the art of polymer chemistry, and need not be described in further detail here. When present, it is preferred that the auxiliary polymer be present at a level of from about 0.10 percent to about 100 percent, preferably from about 1 percent to about 50 percent, more preferably from about 2 percent to about 25 percent by weight, the percentages based on the weight of solids of the primary film-forming polymer present in the composition.

The coating compositions may contain other optional ingredients, for example, anti-settling additives, pigment wetting additives, gassing inhibitors, corrosion inhibitors, anti-foaming additives, surface tension modifiers, mildewcides, rheology modifiers, waxes, metal passivators, UV light absorbers, anti-oxidants, UV light stabilizers, and the like. When present, these additives are generally used at a level of from 0.01 percent to 5 percent by weight, the percentages based on the weight of total solids in the composition, although the amounts may vary according to particular application.

The coating composition can contain other optional ingredients, such as inorganic or organic acids or bases, and the like. When present, these materials are generally used at a level of from about 0.01 percent to about 50 percent, preferably from about 0.10 percent to about 5 percent by weight, the percentages based on the weight of the film-forming polymer used in the coating composition.

The coating compositions may be applied to any of the various substrates to which they adhere, particularly metal. Optionally, the substrate may have been previously coated with a primer coating composition. The compositions can be applied by conventional means, including brushing, dipping, flow coating, spraying and the like, but preferably, they are applied by spraying. The usual spray techniques and equipment for air-spraying can be used.

EXAMPLES

The following examples illustrate several embodiments of the present invention for the sake of describing the best mode of the invention, but it should be understood that the scope of the invention is not limited to these particular embodiments. Examples 1, 3, and 5 illustrate the preparation of unsaturated monoesters from maleic anhydride and various secondary alcohols, and Examples 2, 4, and 6 demonstrate the oxyalkylation of those respective monoesters to form unsaturated hydroxy functional diesters in accordance with the present invention.

Example 1

Preparation of Isopropyl Maleate

A five liter glass reactor equipped with a stirrer, addition funnel, nitrogen atmosphere, reflux condenser, and thermocouple was charged with 1849 grams of maleic anhydride. The solid anhydride was melted by heating to 65° C. Then 1200 grams of 2-propanol were added over 3.5 hours from the addition funnel. After holding another 1.5 hours at 65° C., the temperature was raised to 85° C. and held for 8.75 hours to complete the reaction.

Example 2

Preparation of Isopropyl Hydroxypropyl Maleate 2100 grams of 2-propyl maleate (Example 1), 8.12 grams of triphenylphosphine, and 8.12 grams of tri-2-ethylhexylphosphite were charged to a 4 liter stirred stainless steel pressure autoclave. The reactor was twice pressurized with nitrogen then depressurized, finally leaving 0.36 kPa nitrogen. The reactor contents were heated to 85° C., and 829.74 grams of propylene oxide were added over 3 hours. Then 270 grams of propylene oxide were added. After 3 hours, the pressure was lowered to remove residual propylene oxide. The product was a liquid containing less than 100 parts per million propylene oxide, having a viscosity of 75.7 centipoise at 25° C. and an acid number of 0.61 milligrams KOH/gram of solution.

Example 3

Preparation of 2-Butyl Maleate

A procedure similar to that for isopropyl maleate was followed, substituting an equimolar quantity of 2-butanol for isopropanol.

Example 4

Preparation of 2-Butyl Hydroxypropyl Maleate

Two thousand grams of 2-butyl maleate (Example 3), 5.67 grams of triphenylphosphine, and 5.67 grams of tri-2-ethylhexylphosphite were charged to a 4 liter stirred stainless steel pressure autoclave. The reactor was twice pressurized with nitrogen then depressurized, finally leaving 0.36 kPa nitrogen. The reactor contents were heated to 110° C., and 724 grams of propylene oxide were added over 3 hours. Then 75 grams of propylene oxide were added. After 3 hours, the temperature was reduced to 100° C. and the pressure was lowered to remove residual propylene oxide. The product was a liquid containing less than 100 parts per million propylene oxide and having a viscosity of 172 centipoise at 25° C., density of 1.097 grams per cubic centimeter, and an acid number of 6.1 milligrams KOH/gram of solution.

Example 5

Preparation of Cyclohexyl Maleate

A reactor was charged with 1681 grams of maleic anhydride, which was melted under a nitrogen atmosphere. Then 1818 grams of cyclohexanol was added gradually over 3.3 hours at a reactor temperature of 60 to 65° C. Then the reactor was heated to 85°–90° C. and held for 9.5 hours.

Example 6

Preparation of Cyclohexyl 2-Hydroxypropyl Maleate

In a procedure similar to that for 2-butyl hydroxypropyl maleate (Example 4), 1400 grams of cyclohexyl maleate (Example 5) was converted to cyclohexyl 2-hydroxypropyl maleate by reaction with 449 grams of propylene oxide. The reaction temperature was 85° C., and the reaction time was 1 hour. The vacuum stripping time was 2.5 hours at 80° to 85° C. The reaction product had a viscosity of 785 centipoise at 25° C. and an acid number of 27.3 milligrams of KOH per gram of solution.

In Examples 7 through 10 dimaleate monomers as described above were copolymerized with various olefins to form hydroxy functional polymers that have utility in coating compositions and other applications.

Example 7

Polymerization of Cyclohexyl Hydroxypropyl Maleate and Isobutylene 722 grams of AROMATIC® 100 aromatic solvent blend from Exxon was charged to a four liter autoclave. The autoclave was evacuated and repressurize with nitrogen to 35 kPa, and the evacuation and repressurization were repeated two more times. At 97° C., 147 milliliters of a solution of 189 grams of t-amyl peroctoate and 170.7 grams of AROMATIC 100 was added over 2 hours. During the same 2 hours, 378.5 grams of isobutylene and 1656 grams of cyclohexyl 2-hydroxypropyl maleate (Example 6) were added at a constant rate. Once the feeds above were completed, 147 grams more of the initiator solution was added over 3 hours. Then the reaction temperature of 97° C. was maintained for an additional half hour, whereupon the reactor was cooled and vented. The residual monomer was stripped at 80° C. for 5 hours. The product had a measured solids of 73%, viscosity of 2650 centipoise at 25° C. (Brookfield; spindle number 4 at 12 rpm), number average molecular weight (measured by gel permation chromatography, polystyrene as standard) of 1419, and weight average molecular weight of 4903.

Example 8

Polymerization of Cyclohexyl Hydroxypropyl Maleate, Isobutylene and Dibutyl Maleate In a procedure similar to that for the polymerization of cyclohexyl maleate and isobutylene above, 496 grams of AROMATIC 100 was charged to the autoclave and 175.8 milliliters of a solution of 162 grams of t-amyl peroctoate and 145.6 grams of AROMATIC 100, 597.5 grams of dibutyl maleate, 282 grams of isobutylene, and 491 grams of cyclohexyl 2-hydroxypropyl maleate (Example 6) were charged over 2 hours. During the next two hours, at 97° C., 58.6 milliliters of the initiator solution were added. After an additional half hour, the reactor was cooled and vented. Vacuum stripping resulted in a product of 68% solids with a viscosity of 314 centipoise at 25° C. (Brookfield; spindle number 2 at 60 rpm). The acid value was 3.8 milligrams KOH/gram of solution. The monomer content was 0.29% cyclohexyl 2-hydroxypropyl maleate and 1.07% dibutyl maleate of the final solution.

Example 9

Polymerization of Cyclohexyl Hydroxypropyl Maleate and 1-Hexene

To a 4 liter stirred stainless steel autoclave 722 grams of AROMATIC 100 and 737 grams 1-hexene were charged. Following nitrogen purging, and leaving a low nitrogen pressure (0.36 kPa) on the autoclave, then heating to 97° C., the following were fed to the reactor over 2 hours: 147 milliliters of a solution of 189 grams t-amyl peroctoate and 171 grams AROMATIC 100, and 1122 grams cyclohexyl 2-hydroxypropyl maleate (Example 6). Then an additional 147 milliliters of the initiator solution were added over 3 hours. After an additional hold at the reaction temperature of 97° C., the reactor was cooled. The reaction product had a measured solids of 57.3%, and a viscosity of 54.9 centipoise at 25° C. (Brookfield; spindle number 1 at 60 rpm).

Example 10

Polymerization of Cyclohexyl Hydroxypropyl Maleate and 1-Decene

In a polymerization similar to that above, the copolymer was formed under the following reaction parameters:

Solvent: 496 grams toluene

Initiator solution: 192 grams t-amyl peroctoate and 146 grams toluene

Three hour feeds:

176 milliliters initiator solution 682 milliliters 1-decene 791 grams cyclohexyl 2-hydroxypropyl maleate (Example 6)

Reaction Temperature: 97° C.

Two hour post feed: 58.6 milliliters initiator solution

Hold time following initiator feed: 0.5 hour.

The product solids were 51.7%, and the viscosity was 30.2 centipoise at 25° C. (Brookfield; spindle number 1 at 60 rpm). The acid value of the product was 6.1 milligrams KOH per gram of solution.

All of the polymer products of Examples 7 to 10 had a Gardner color of 1 or less than 1.

Stability Test for Monomaleate Esters

A series of maleate monoesters (Examples 11 through 14) was prepared from the following alcohols: ethyl alcohol (Example 11), n- propyl alcohol (Example 12), n-hexyl alcohol (Example 13), and isopropyl alcohol (Example 14) by techniques similar to that used for isopropyl maleate in Example 1. During the preparation of these maleate monoesters the temperature was no higher than 65° C. Each of the monoesters was heated for 64 hours at 60° C., then analyzed by $^{13}C$ NMR. The carbonyl region was integrated to determine the relative amounts of maleic acid, monoester, diester, and maleic anhydride present both before and after heating. The results are presented in Table III.

Immediately following heating, all samples were liquid, however on standing, the n-hexyl maleate sample contained a precipitate which was identified as largely maleic acid by NMR. The conclusion reached from the data is that the secondary isopropyl maleate is stable at the 60° C. temperature for extended periods, whereas the primary alcohols (ethyl, n-propyl, and n-hexyl) disproportionate into maleic acid and dialkyl maleates.

TABLE III

Stability Test for Maleate Monoesters

| | | Mole % | | | |
|---|---|---|---|---|---|
| Example | Ester Type | Maleic Acid | Monomaleate Ester | Dimaleate Ester | Maleic Anhydride |
| Before Heating (RT Control) | | | | | |
| 11 | Ethyl | 6.07 | 76.87 | 17.04 | 0.00 |
| 12 | n-Propyl | 7.36 | 83.96 | 8.24 | 0.42 |
| 13 | n-Hexyl | 7.08 | 83.81 | 9.09 | 0.00 |
| 14 | Isopropyl | 4.70 | 90.67 | 2.76 | 1.84 |
| After Heating (64 hours at 60 C.) | | | | | |
| 11 | Ethyl | 11.456 | 64.747 | 23.796 | 0.000 |
| 12 | n-Propyl | 9.451 | 74.882 | 15.304 | 0.364 |
| 13 | n-Hexyl | 7.001 | 77.639 | 12.903 | 2.456 |
| | Solid: | 51.340 | 41.571 | 7.090 | 0.000 |
| 14 | Isopropyl | 4.439 | 90.673 | 2.377 | 2.511 |

Coating Composition

Example 15 illustrates a two-package, polyisocyanate cured coating composition incorporating the unsaturated hydroxy functional diester copolymer of the present invention.

Example 15

A two-package coating composition may be formulated with the copolymer of Example 7 as follows:

| | Weight |
|---|---|
| PACKAGE 1 | |
| Example 7 Copolymer | 45.01 |
| Dibutyl tin dilaurate[1] | 0.023 |
| Toluene | 1.197 |
| TINUVIN 384[2] | 1.506 |
| BYK 300[3] | 0.254 |
| EKTASOLVE EEP[4] | 29.85 |
| Sub Total | 77.84 |
| PACKAGE 2 | |
| HDT-LV polyisocyanate[5] | 22.16 |
| Total | 100.000 |

[1]Dibutyl tin dilaurate is a catalyst available from ATOCHEM North America, Philadelphia, Pennsylvania.
[2]TINUVIN 384 is a UV absorber available from Ciba-Geigy Corporation, Hawthorne, New York.
[3]BYK 300 is an additive available from BYK-Chemie USA Wallingford, Connecticut.
[4]EKTASOLVE EEP is a solvent available from Eastman Chemical Products Kingston, Tennessee.
[5]HDT-LV is a low viscosity hexane diisocyanate trimer available from Rhône-Poulenc Inc., Fine Organics Division, Cranbury, New Jersey.

Example 16

A one package composition was formulated with the polymer of Example 7 as follows:

| Ingredient | Weight(grams) |
| --- | --- |
| Methyl amyl ketone | 5.0 |
| Xylene | 11.0 |
| 2-Butoxyethanol acetate | 4.0 |
| TINUVIN ® 900 UV absorber[1] | 1.5 |
| Tinuvin ® 328 UV absorber[1] | 1.5 |
| CYMEL ® 1130 melamine resin[2] | 37.0 |
| Poly(butylacrylate) flow agent[3] | 0.7 |
| AROMATIC 100 ® solvent[4] | 10.1 |
| Microgel flow control additive[5] | 2.8 |
| Resin from Example 7 | 84.7 |
| Ethanol | 6.0 |
| TINUVIN ® 292 light stabilizer[1] | 0.4 |
| Dodecylbenzene sulfonic acid (70% in xylene) | 1.0 |

[1] Available from Ciba-Geigy
[2] Available from CYTEC Industries
[3] Poly(butylacrylate), Mn = 2660, Mw = 6700; 62.5% solids in xylene.
[4] Available from Exxon Chemical Co.
[5] Acrylic microgel flow modifier made according to Example 1 1 of U.S. Pat. No. 4,147,688

The ingredients were added sequentially with stirring, then sprayed onto an uncured, compatible basecoat (DCT-6373 black, available from PPG Industries). The steel panel containing the coatings was baked for 25 min. at 140 degrees C. after a 10 minute flash time at room temperature to allow for solvent evaporation. The resulting clear coating was 43 micrometers in thickness, over the black basecoat of 17 micrometers. The coatings had a pencil hardness of 2H (according to ASTM method D 3363-92a), both before and immediately after a 2.5 centimeter diameter xylene spot was wiped from the coating surface after it resided on the suface for 3 minutes) which corresponds to excellent xylene resistance, and a distinctness of image (DOI) of 93.5 as measured by a Hunter Dorigon II DOI Meter).

The invention has been set forth in connection with specific embodiments for the sake of disclosing the best mode for carrying out the invention. However, it should be understood that other variations and modifications as are known to those of skill in the art may be resorted to without departing from the scope of the invention as defined by the following claims.

We claim:

1. A hydroxy functional, unsaturated maleate diester comprising the esterification reaction product of an unsaturated anhydride with a secondary alcohol component comprising cylohexanol to form a maleate monoester, followed by oxyalkylation of the maleate monoester with an epoxy compound whereby a maleate diester is formed with hydroxy functionality.

2. The compound of claim 1 wherein the anhydride is selected from the group consisting of maleic anhydride, citraconic anhydride, and mixtures thereof.

3. The compound of claim 1 wherein the secondary alcohol component further comprises at least one compound selected from the group consisting of 2-propanol, 2-butanol and mixtures thereof.

4. The compound of claim 1 wherein the secondary alcohol component consists essentially of cyclohexanol.

5. The compound of claim 1 wherein the epoxy compound comprises an alkylene oxide.

6. The compound of claim 5 wherein the alkylene oxide consists essentially of propylene oxide.

7. A hydroxy functional, unsaturated maleate diester comprising the esterification reaction product of maleic anhydride with cyclohexanol to form a maleate monoester, followed by oxyalkylation of the maleate monoester with an alkylene oxide whereby a maleate diester is formed with hydroxy functionality.

8. The compound of claim 7 wherein the alkylene oxide is propylene oxide.

* * * * *

UNITED STATES PATENT AND TRADEMARK OFFICE
CERTIFICATE OF CORRECTION

PATENT NO. : 5,750,770

DATED : May 12, 1998

INVENTOR(S) : Edward E. McEntire, et al.

It is certified that error appears in the above-identified patent and that said Letters Patent is hereby corrected as shown below:

Claim 1, line 4:    Delete [cylohexanol] and insert --cyclohexanol--

Signed and Sealed this

Twenty-first Day of July, 1998

Attest:

BRUCE LEHMAN

Attesting Officer

Commissioner of Patents and Trademarks